(12) United States Patent
Amino

(10) Patent No.: US 12,376,866 B2
(45) Date of Patent: Aug. 5, 2025

(54) THIN-BLADE CHISEL SYSTEM

(71) Applicant: Medmetalex Co., Ltd., Osaka (JP)

(72) Inventor: Hirokazu Amino, Osaka (JP)

(73) Assignee: Medmetalex Co., Ltd., Osaka (JP)

( * ) Notice: Subject to any disclaimer, the term of this patent is extended or adjusted under 35 U.S.C. 154(b) by 536 days.

(21) Appl. No.: 17/612,786

(22) PCT Filed: Nov. 16, 2020

(86) PCT No.: PCT/JP2020/042595
§ 371 (c)(1),
(2) Date: Nov. 19, 2021

(87) PCT Pub. No.: WO2021/229845
PCT Pub. Date: Nov. 18, 2021

(65) Prior Publication Data
US 2022/0240948 A1    Aug. 4, 2022

(30) Foreign Application Priority Data
May 15, 2020 (JP) ................... 2020-085690

(51) Int. Cl.
*A61B 17/16* (2006.01)
*A61F 2/46* (2006.01)

(52) U.S. Cl.
CPC ...... *A61B 17/1604* (2013.01); *A61B 17/1666* (2013.01); *A61B 17/1668* (2013.01); *A61F 2/4607* (2013.01)

(58) Field of Classification Search
CPC . A61B 17/1604; A61B 17/1668; A61B 17/92; A61B 17/921; A61B 2017/922;
(Continued)

(56) References Cited

U.S. PATENT DOCUMENTS 4,979,574 A    12/1990 Lalama
5,423,825 A *   6/1995 Levine .................. A61F 2/4611
                                          606/86 R
(Continued)

FOREIGN PATENT DOCUMENTS

JP          5-63511 U1    8/1993
WO    WO-0154607 A1 *     8/2001  ........... A61C 8/0089

OTHER PUBLICATIONS

Machine translation of WO 0154607, obtained from https://worldwide.espacenet.com/ Jun. 6, 2024. (Year: 2024).*

*Primary Examiner* — Amy R Sipp
(74) *Attorney, Agent, or Firm* — Howson & Howson LLP

(57) ABSTRACT

A thin-blade chisel system, for separating an outer surface of an orthopedic implant and an inner surface of a bone from each other, includes a thin-blade chisel having a blade tip at a distal end portion in a longitudinal direction, and a hammering direction changing tool engaged with the thin-blade chisel to apply a force in an advancing direction of the blade tip. The thin-blade chisel includes a hammering blow-receiving part, preferably a through hole penetrating in a thickness direction, at a predetermined position on a proximal side closer to the surgeon. The hammering direction changing tool includes a hammering portion to be hammered, located at a proximal end portion, and a recess formed at a distal end portion, to be engaged with an inner circumferential surface of the through hole.

3 Claims, 25 Drawing Sheets

(58) Field of Classification Search
CPC .............. A61B 2017/924; A61F 2/4603; A61F 2/4607; A61F 2002/4641; A61F 2002/4681
See application file for complete search history.

(56) References Cited

U.S. PATENT DOCUMENTS

| | | |
|---|---|---|
| 6,126,664 A | 10/2000 | Troxell et al. |
| 2002/0165550 A1 | 11/2002 | Frey et al. |
| 2003/0139747 A1 | 7/2003 | Wolff et al. |
| 2004/0117020 A1 | 6/2004 | Frey et al. |
| 2011/0213370 A1 | 9/2011 | Nakamura |
| 2012/0290020 A1 | 11/2012 | Meridew |
| 2014/0336656 A1 | 11/2014 | Rogers et al. |
| 2018/0206859 A1* | 7/2018 | Pendleton .......... A61B 17/1637 |

* cited by examiner

THIN-BLADE CHISEL SYSTEM

FIELD OF THE INVENTION

The present invention relates to a thin-blade chisel system for separating an outer surface of an orthopedic implant planted inside a bone, and the inner surface of the bone, from each other. The present invention also relates to the thin-blade chisel and a hammering direction changing tool employed in the system.

BACKGROUND OF THE INVENTION

Various types of artificial joints for curing a disease of a joint, such as a hip joint or a knee joint, and also artificial bones for curing bones other than the joint, have been developed, and are employed for actual clinical treatment. For example, an orthopedic implant, called a fully artificial hip joint, is employed for treatment of a disease of coxarthrosis, and in this case a hip joint stem (orthopedic implant) to be planted in a femur medullary cavity in place of the excised femur is employed, and a semispherical shell (orthopedic implant) is fixed to an acetabular roof, reamed in a dome shape, on the side of the acetabular roof of the pelvis.

In the orthopedic surgery, the implant buried in the bone of the patient and the bone have to be firmly fixed to each other. When the combination of the implant and the bone becomes insufficient after the surgery, and is loosened even a little, pain may be provoked. To prevent the combination from becoming loose for a long time after the surgery, for example, a metal roughened surface coating is applied, and also a guided bone regeneration material such as calcium hydroxyphosphate (apatite) is coated over the surface of the stem to be buried in the femur. After the stem is buried in the femur, the cells of the bone intrude into the dips and bumps on the surface of the stem, by which the implant and the bone are firmly fixed to each other.

Depending on the case, the implant can be firmly fixed to the bone, for example by applying an orthopedic bone cement (resin) between the stem and the inner wall of the medullary cavity, or between the shell and the acetabular roof, even though the roughened surface coating and the guided bone regeneration material are not employed.

FIG. 1 illustrates a fully artificial hip joint, the orthopedic implants of which are buried in a femur 1 and a pelvis 2. A hip joint stem 3 is buried in the femur 1, and an acetabular roof-side implant, formed by combining a metal shell 10 and a resin liner 9, is attached to the pelvis 2. On the hip joint stem 3 made of a metal, the roughened surface coating and the guided bone regeneration material (dotted portion) are applied to a proximal portion 4, and a distal portion 5 is deeply buried in the medullary cavity. A neck portion 6 and a tapered portion 7 are formed in the upper portion of the hip joint stem 3, and a caput sphere 8 is taper-fitted on the tapered portion 7. The caput sphere 8 and the resin liner 9 slide relative to each other, thus constituting the joint. Here, regarding the limbs, a portion closer to the body trunk will be referred to as a proximal portion, and a farther portion will be referred to as a distal portion.

FIG. 2 illustrates a cross-section of the hip joint stem 3 buried in the femur 1. Gap portions illustrated between the outer surface of the hip joint stem 3 and the inner surface of the femur 1 represent bone-conglutinated parts 13, where the hip joint stem 3 and the inner surface of the femur 1 are firmly conglutinated, via an osteoblast or bone cement. The area around the proximal portion 4 has a large contact surface area, and therefore excising the corresponding portions of the bone-conglutinated part 13 enables the hip joint stem 3 to be extracted.

SUMMARY OF THE INVENTION

In the field of orthopedic surgery, in general, the surgery that a patient undergoes for the first time is called a primary surgery, and the surgery operated again on the same part of the same patient is called a revision surgery. The revision surgery may become necessary, owing to the loosening of the implant after the surgery, infection of the operated part, or a disease of another part of the patient. When it becomes necessary to perform the revision surgery, first the implant buried in the primary surgery has to be extracted from the bone. Since the implant is firmly combined with the bone, it is not easy to separate the outer surface of the implant and the inner surface of the bone from each other. To separate the outer surface of the implant and the inner surface of the bone from each other, a thin-blade chisel is widely employed.

However, the implant has various curved surfaces. Accordingly, an existing thin-blade chisel often fails to separate the outer surface of the implant and the inner surface of the bone from each other efficiently, quickly, and safely, owing to discordance in shape from the gap, or a damage in the bone resultant from the use of the chisel while neglecting the discordance. In many such cases, additional trouble and time are required, for the restoration of the damaged bone. An inner portion of the proximal portion 4 is called a proximal inner portion 11, and an outer portion is called a proximal outer portion 12. In the example of FIG. 2, the cross-section of the proximal inner portion 11 is curved, while the proximal outer portion 12 has a straight shape. Here, the inner portion refers to a portion closer to the center vertical line of the human body, and the outer portion refers to a portion farther from the center vertical line of the human body.

FIG. 24 schematically illustrates an existing thin-blade chisel 100 about to extract the hip joint stem 3. The thin-blade chisel 100 includes a hammering portion 103, a handle 102, a holding shaft portion 101, a shaft portion 104, and a blade tip 105. The hip joint stem 3 planted in the primary surgery can be extracted, by hitting the hammering portion 103 with a hammer to apply a force F, so as to make the leading end of the blade tip 105, and edges on the respective sides close to the leading end, bite into the proximal inner portion 11, thereby cutting apart the bone-conglutinated part 13 adhered to the proximal inner portion 11 of the hip joint stem 3.

However, as shown in FIG. 25, the direction of the force F is deviated by an angle θ from a direction P in which the blade tip 105 is supposed to advance, and therefore the direction of the applied force F is deviated from the direction of the gap. Accordingly, in order to make the directions accord with each other, it is necessary to hammer the thin-blade chisel at an optimum timing, while applying a force in a direction perpendicular to the advancing direction. However, when the hammering timing is wrong, the bone or the thin-blade chisel itself may be broken, and therefore efficiently and safely cutting the bone-conglutinated part 13 apart is an extremely difficult job that requires high expertise.

Accordingly, the present invention provides a thin-blade chisel system, capable of efficiently cutting apart an interface between an implant and a bone firmly combined to each other, and preventing the bone from being damaged, thereby efficiently separating the implant and the bone from each other.

In a first aspect, the present invention provides a thin-blade chisel system for separating an outer surface of an orthopedic implant planted inside a bone, and an inner surface of the bone from each other. The thin-blade chisel system includes a thin-blade chisel having a blade tip with an edge formed at an end portion in a longitudinal direction, on a distal side distant from a surgeon, and a hammering direction changing tool engaged with the thin-blade chisel to apply a force in an advancing direction of the blade tip. The thin-blade chisel includes a through hole penetrating in a thickness direction, formed at a predetermined position in a vicinity of the blade tip, and on a proximal side closer to the surgeon. The hammering direction changing tool includes a hammering portion to be hammered, located at a proximal end portion, and a recess formed at a distal end portion, to be engaged with an inner circumferential surface of the through hole. By hammering the hammering portion, with the recess of the hammering direction changing tool engaged with the through hole of the thin-blade chisel at a predetermined angle, the edge of the thin-blade chisel can intrude in accordance with different curve directions of the inner surface of the bone.

With the thin-blade chisel system according to the first aspect of the present invention, the edge of the chisel can be made to intrude in accordance with the different curve directions of the inner surface of the bone, and therefore the edge can advance along the interface between the implant and the bone firmly combined to each other. Unlike the existing thin-blade chisel, this system eliminates the need to make the edge advance while applying a force in the direction perpendicular to the advancing direction, so as to change the orientation of the edge successively along the direction of the gap, thereby minimizing the likelihood that the bone and the thin-blade chisel are damaged by an excessive force applied during such operation. As a result, the implant and the bone can be separated from each other, accurately and quickly. The front-view shape of the through hole is not limited to circular, but may be elliptical, or a polygonal shape such as square.

In a second aspect, the present invention provides the thin-blade chisel system according to the first aspect, in which the hammering direction changing tool includes an extracting projection to be inserted in the through hole, formed in a vicinity of the recess, and a bar-shaped handle formed in a vicinity of the hammering portion, so as to extend in a direction perpendicular to a longitudinal axis of the hammering direction changing tool, so that the thin-blade chisel can be extracted, by inserting the extracting projection into the through hole, and hammering the handle from the distal side toward the proximal side.

In the thin-blade chisel system according to the second aspect of the present invention, the hammering direction changing tool includes the extracting projection to be inserted in the through hole, formed in the vicinity of the recess, and also the bar-shaped handle formed in the vicinity of the hammering portion, so as to extend in the direction perpendicular to the longitudinal axis of the hammering direction changing tool. Accordingly, the thin-blade chisel that has deeply intruded into the bone can be easily extracted, by inserting the extracting projection into the through hole, and hammering the handle from the distal side toward the proximal side. In the case of the existing thin-blade chisel without the hammering direction changing tool, a handle provided on the chisel itself has to be hammered, from the distal side toward the proximal side. In this case, the thin-blade chisel that has deeply intruded into the fine gap in the femur has to be hammered in a direction different from the direction of the gap, and therefore not only the bone, but also the thin-blade chisel, is often broken. Therefore, a secondary job is required, such as destroying the corresponding portion of the bone, in order to extract the leading end of the blade tip, which has been broken and separated. Moreover, it is no longer possible to bury a new implant, on the base bed of the bone that has been broken to a large extent. However, the second aspect of the present invention eliminates such drawbacks.

A third aspect of the present invention provides the thin-blade system according to the first aspect, in which the thin-blade chisel further includes a simulation piece having a portion of a same shape as the blade tip, located at a same position as the blade tip in the longitudinal direction, and oriented parallel to the blade tip, with a predetermined spacing therefrom.

The thin-blade chisel system according to the third aspect of the present invention can additionally include the simulation piece having the same shape as the blade tip, and located at the same position as the blade tip in the longitudinal direction, parallel to the blade tip with a predetermined spacing therefrom. Therefore, although the position of the leading end of the blade tip that has intruded into the bone is unable to be recognized visually, the simulation piece having the same shape, and located at the same position as the blade tip, enables the surgeon to confirm visually to which position the leading end of the blade tip of the thin-blade chisel has reached, during the surgery. Such an arrangement not only enables the surgeon to confirm whether the leading end of the blade tip has reached the target position, but also prevents the thin-blade chisel from being made to intrude too deeply into the bone, thereby preventing the bone and the chisel from being damaged.

A fourth aspect of the present invention provides the thin-blade chisel system according to the third aspect, in which the simulation piece includes a light emitting element provided at a distal end portion.

In the thin-blade chisel system according to the fourth aspect of the present invention, the simulation piece includes the light emitting element provided at the distal end portion, for a portion of the diseased part dark and difficult to see during the surgery. Therefore, the surgeon can quite easily recognize the position of the leading end of the blade tip of the thin-blade chisel, with the assistance of the light emitting element.

The invention has the following advantageous effects. According to the present invention, a force can be applied to the blade tip in a direction other than the axial direction of the thin-blade chisel, and therefore the interface between the implant and the bone firmly combined to each other can be efficiently and safely cut apart. Accordingly, the implant and the bone can be efficiently and safely separated from each other, and also the bone can be preserved free from damage. As a result, the likelihood of success of the revision surgery to insert a new implant is significantly increased, which is quite beneficial to the patients.

DETAILED DESCRIPTION

Hereafter, embodiments of the present invention will be described in detail, with reference to the drawings. It should be noted that the following embodiments are essentially preferable examples, and not intended to limit the object to which the present invention is applied, or the scope of its use.

FIG. 3 to FIG. 8 illustrate a thin-blade chisel system according to a first embodiment, and a thin-blade chisel, a hammering direction changing tool, and so forth employed in the first embodiment.

Figure 1:
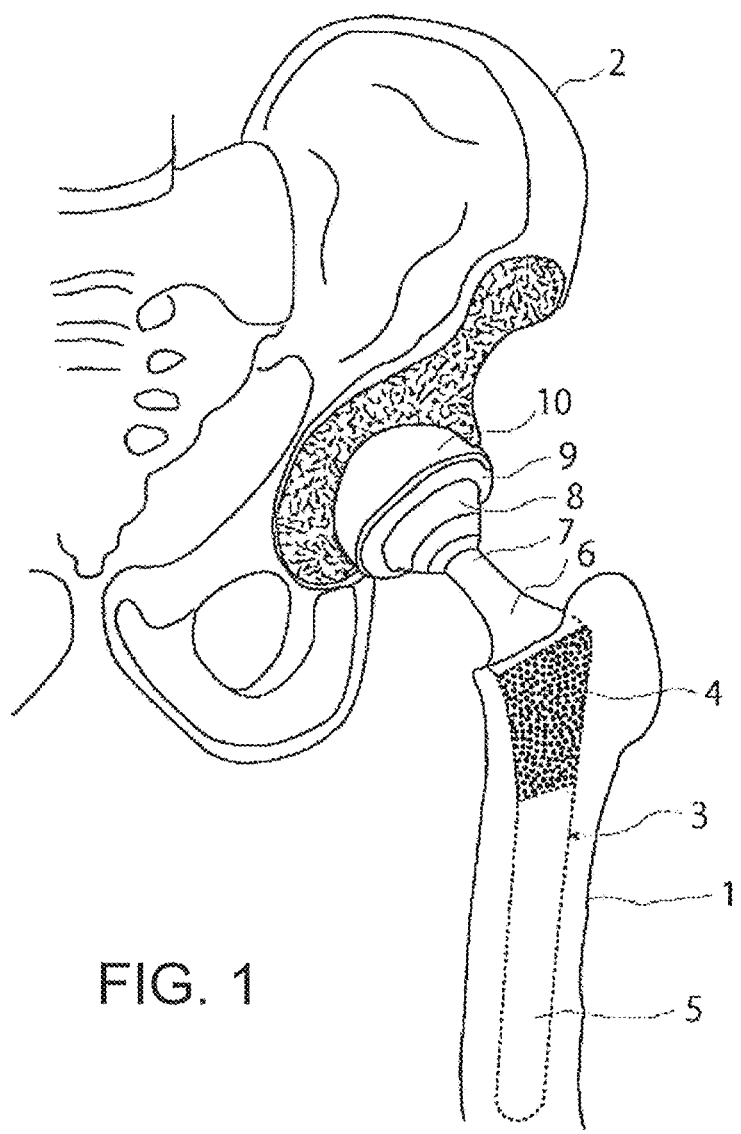
FIG. 1 is a schematic drawing showing an existing fully artificial hip joint, transplanted to a femur and a pelvis.
Figure 2:
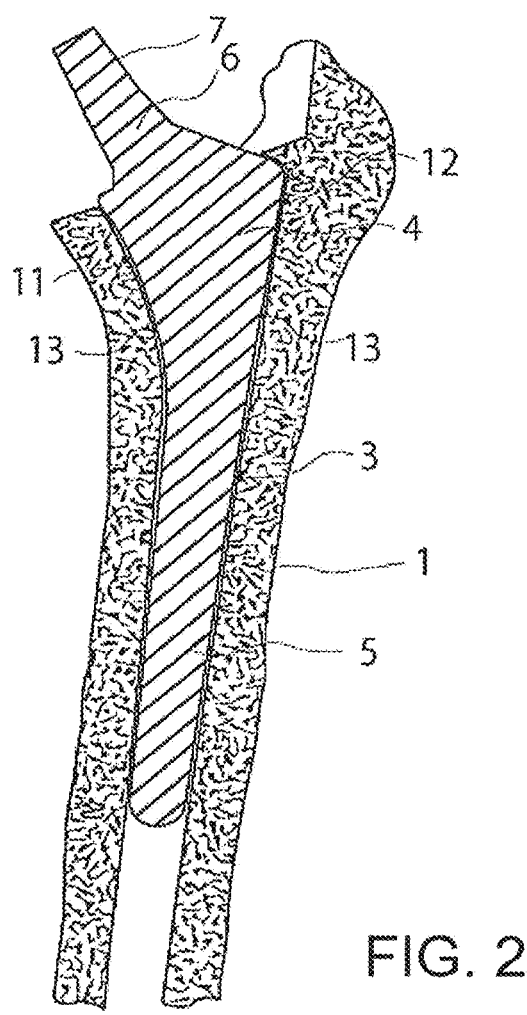
FIG. 2 is a cross-sectional view showing a state where a hip joint stem is buried in the femur.
Figure 3:
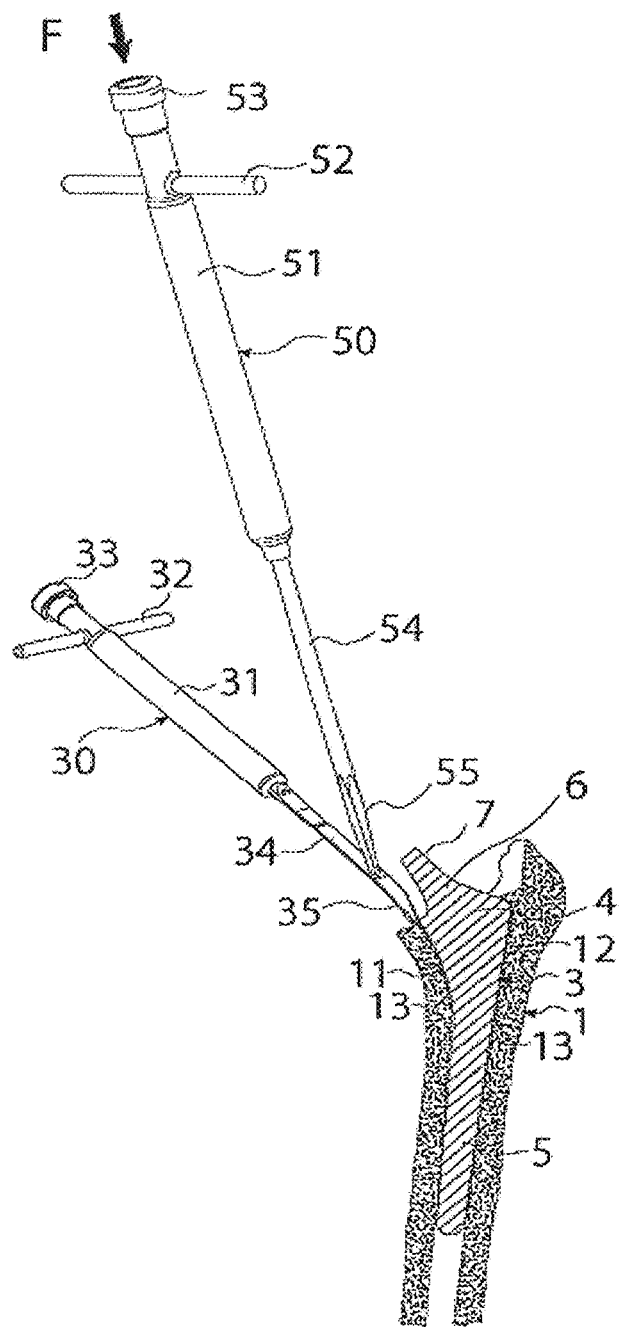
FIG. 3 is a schematic drawing showing the thin-blade chisel system according to an embodiment of the present invention, about to start separating an interface between an inner proximal portion of the hip joint stem and the bone.

The thin-blade chisel 30 in the thin-blade chisel system includes a hammering portion 33, a handle 32, a holding shaft portion 31, a shaft plate 34, and a blade tip 35. The blade tip 35 is curved so as to tilt forward. This curve is formed in accordance with the curve of the proximal inner portion 11, and various patterns are prepared for different shapes of the implant. For the proximal outer portion 12, a straight blade is employed, instead of the one tilted forward as shown in FIG. 3. The shaft plate 34, continuous with the blade tip 35, is removably attached to the holding shaft portion 31.

Figure 4:
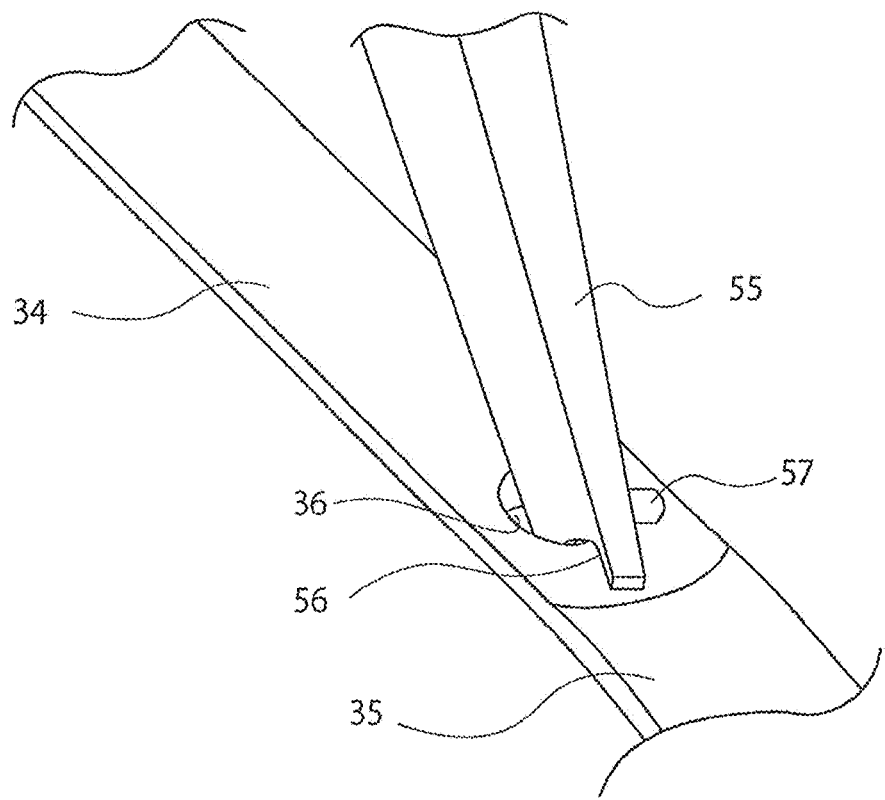
FIG. 4 is an enlarged perspective view showing a recess at the leading end of a hammering direction changing tool, engaged with a through hole of a thin-blade chisel.

The hammering direction changing tool 50 includes a hammering portion 53, a handle 52, a holding shaft portion 51, a leading shaft portion 54, and a leading end portion 55. A recess 56 is formed at the tip portion of the leading end portion 55 as shown in FIG. 4, and the recess 56 is engaged with the inner circumferential surface of a through hole 36 of the thin-blade chisel 30. When the hammering portion 53 is hit by a hammer or the like, a force F is applied in the axial direction of the hammering direction changing tool 50. An extracting projection 57 is formed in the vicinity of the recess 56.

Figure 5:
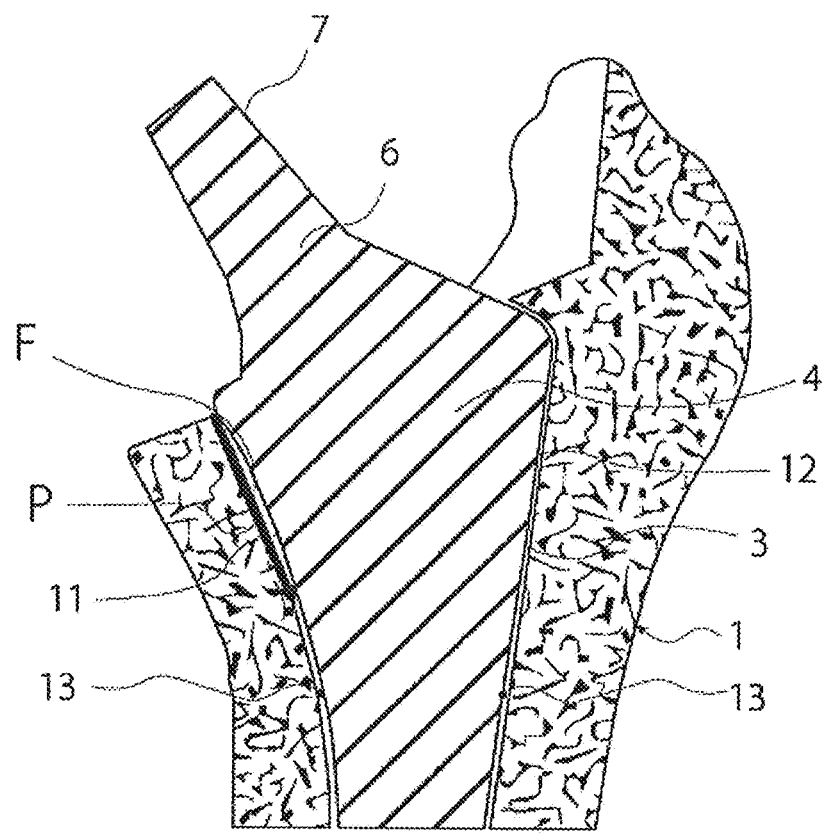
FIG. 5 is a schematic drawing showing a direction in which a force F is applied, and an intruding direction P of the blade tip, when the interface between the inner proximal portion of the hip joint stem and the bone is separated, using the thin-blade chisel system according to the embodiment of the present invention.

FIG. 5 illustrates the direction in which the force F is applied, and a direction P in which the blade tip 35 advances, when the bone-conglutinated part 13 is cut apart with the thin-blade chisel system according to this embodiment, and the direction of F and the direction of P accord with each other in this case. Aligning thus the direction of F and the direction of P allows the implant to be efficiently separated from the bone.

Figure 6:
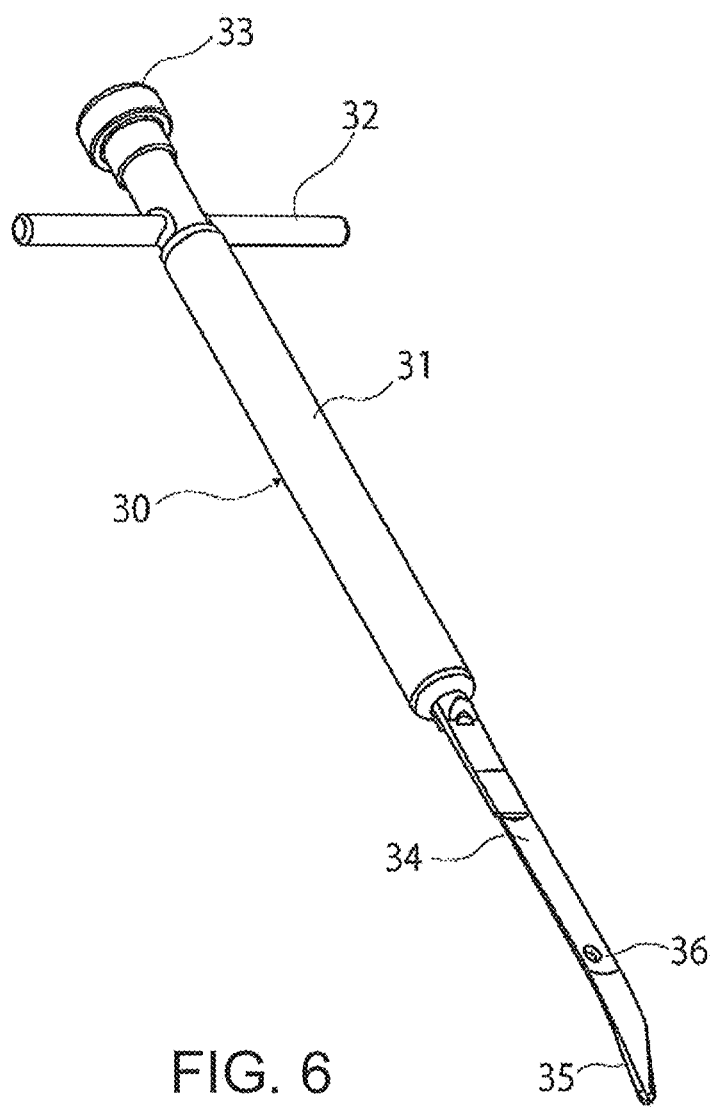
FIG. 6 is a perspective view showing a thin-blade chisel employed in the thin-blade chisel system according to the embodiment of the present invention.
Figure 7:
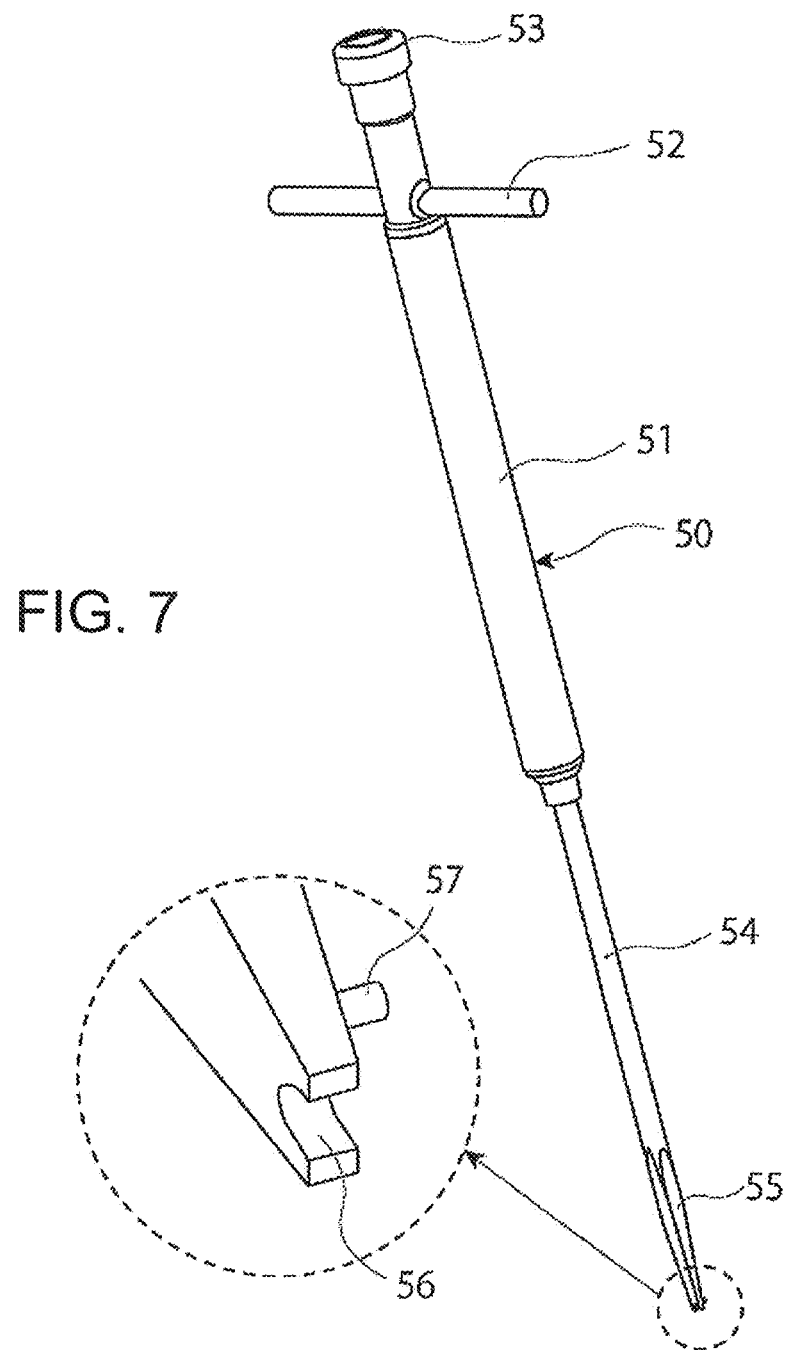
FIG. 7 is a perspective view showing a hammering direction changing tool employed in the thin-blade chisel system according to the embodiment of the present invention.

FIG. 6 is a perspective view showing the thin-blade chisel 30, employed in the thin-blade chisel system according to the first embodiment, and FIG. 7 is a perspective view showing the hammering direction changing tool 50, employed in the thin-blade chisel system according to the first embodiment.

Figure 8:
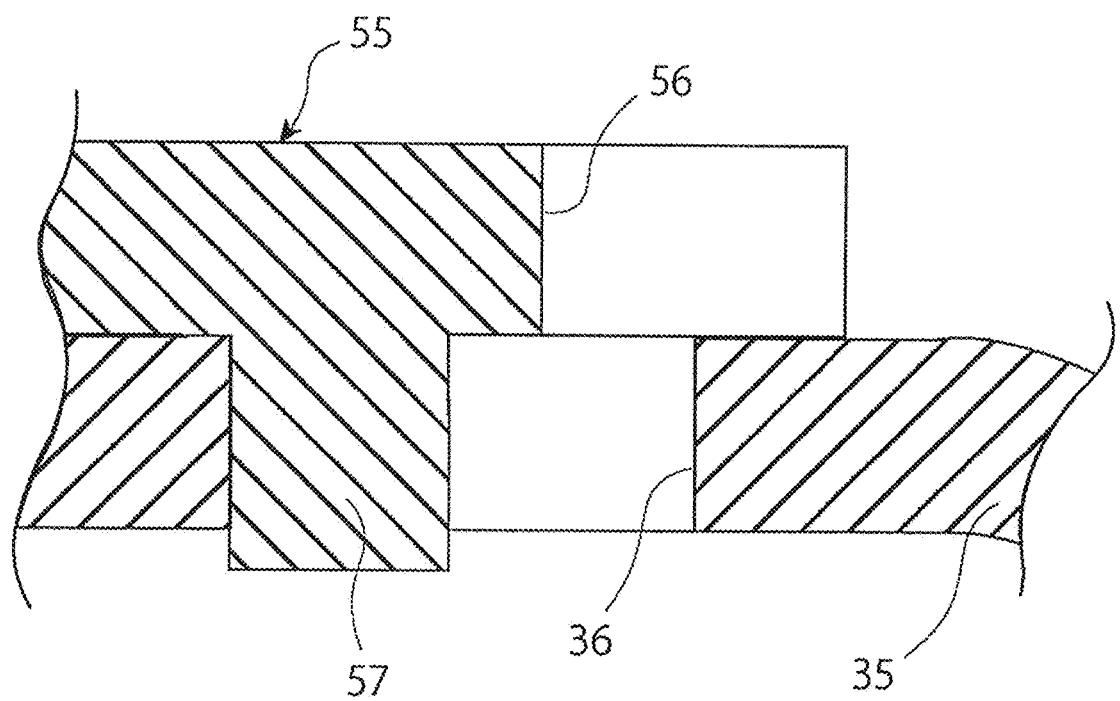
FIG. 8 is a schematic cross-sectional view showing an extracting projection of the hammering direction changing tool inserted in the through hole of the thin-blade chisel, when the thin-blade chisel is to be drawn out from the femur.

FIG. 8 schematically illustrates the blade tip 35 of the thin-blade chisel 30 that has intruded into a medullary cavity, about to be extracted. Although it is possible to extract the thin-blade chisel 30 by hammering the handle 32 from the distal side toward the proximal side, in this case the hammering direction and the direction in which the chisel is to be extracted are different from each other. In the case where the chisel is extracted in this state, the bone or the blade tip of the chisel may be broken, which causes a big problem. However, inserting the extracting projection 57 of the hammering direction changing tool 50 into the through hole 36 of the thin-blade chisel 30, so as to be engaged therewith, and hammering the handle 52 of the hammering direction changing tool 50 from the distal side toward the proximal side, enables the chisel to be extracted with the force applied along the direction of the curve of the conglutinated part, which has thus far been impossible, and prevents the bone and the blade tip of the chisel from being damaged, when the chisel is extracted. Consequently, the blade tip 35 can be extracted from the medullary cavity more easily and more safely.

Figure 9:
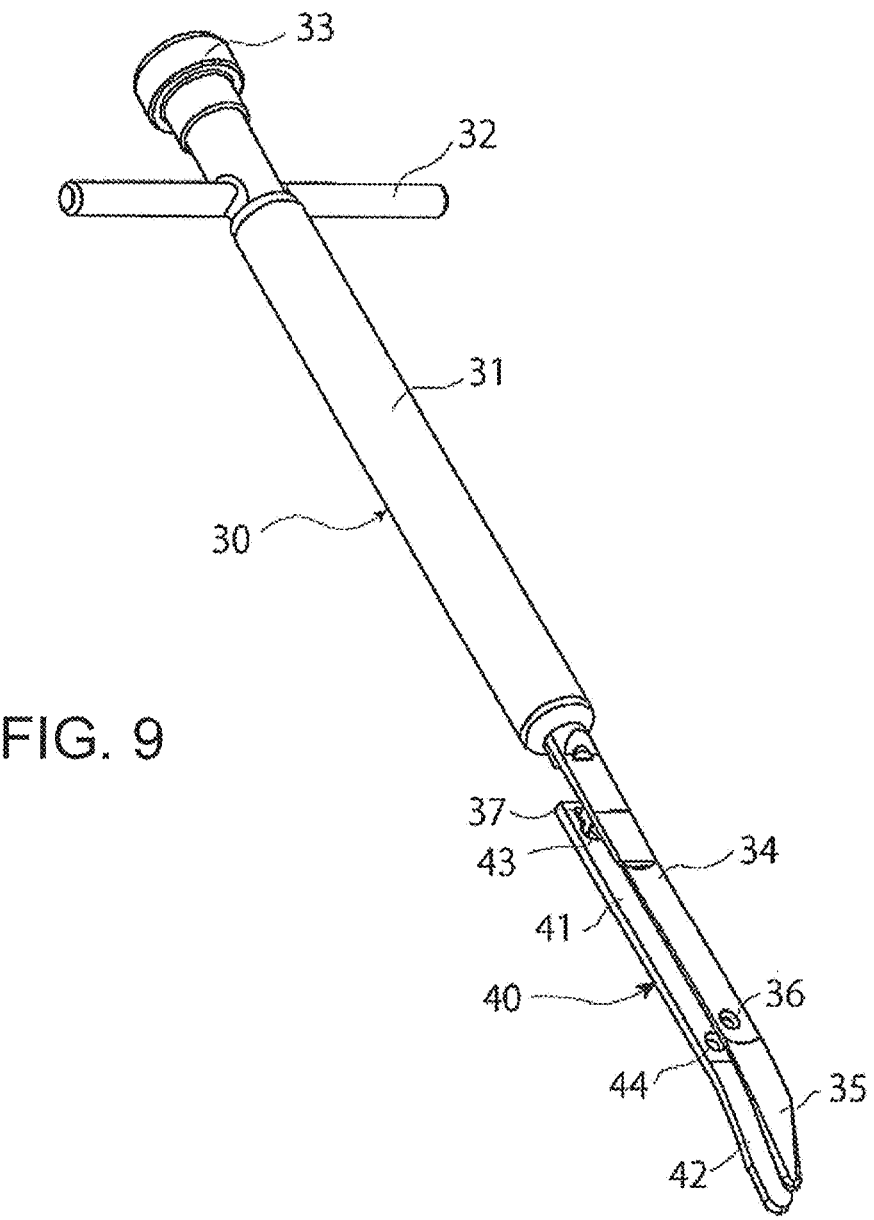
FIG. 9 is a perspective view showing the thin-blade chisel, with a simulation piece attached thereto.
Figure 10:
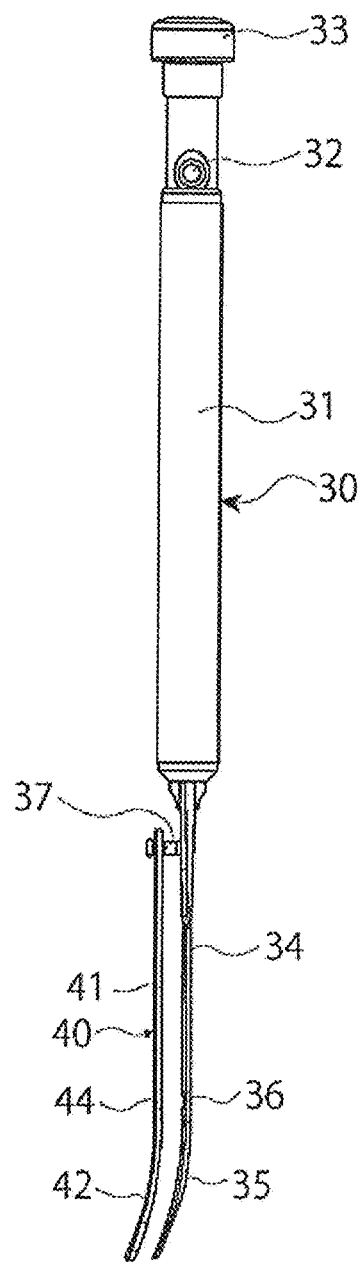
FIG. 10 is a side view showing the thin-blade chisel, with the simulation piece attached thereto.
Figure 11:
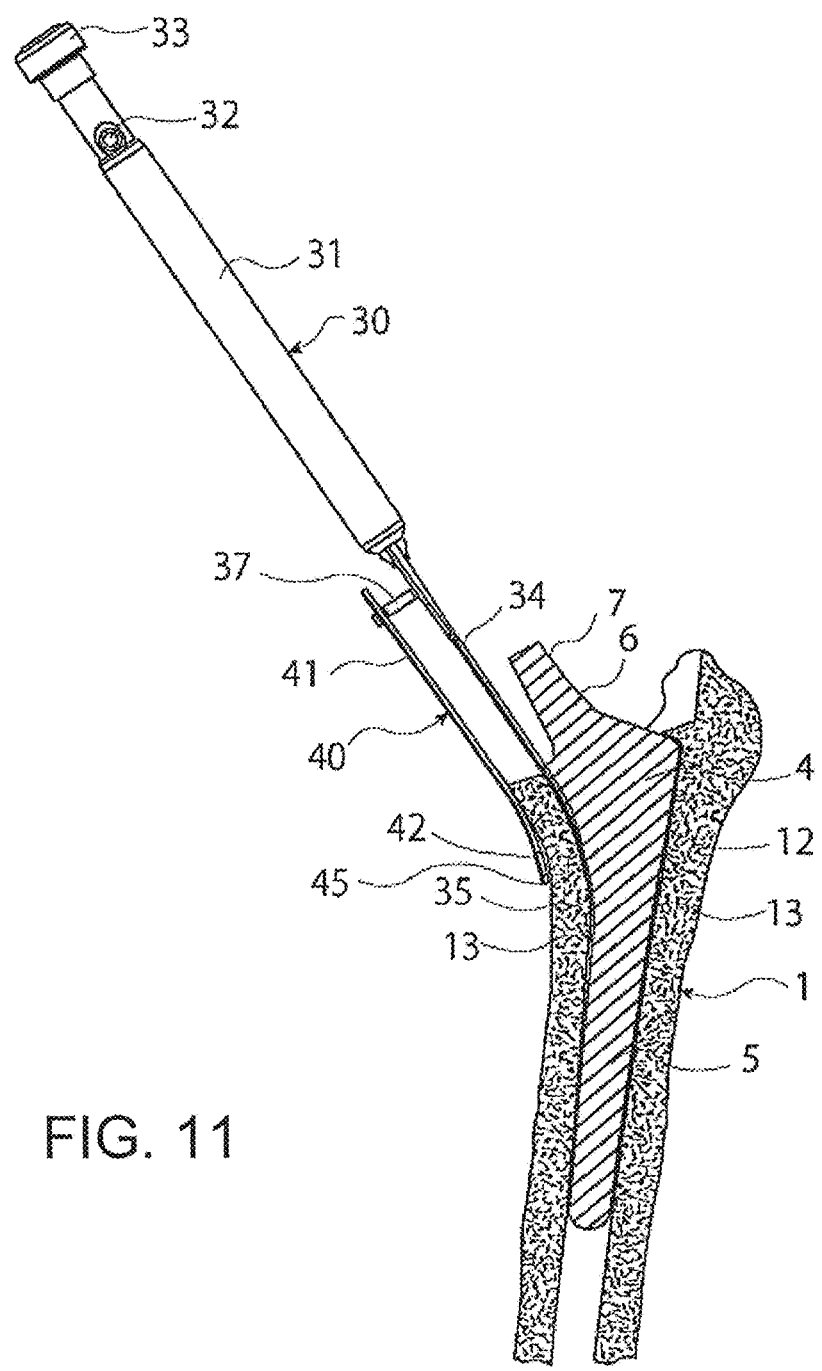
FIG. 11 is a schematic drawing showing a state where the thin-blade chisel with the simulation piece has intruded into inside of the femur.

FIGS. 9 to 11 illustrate the thin-blade chisel system according to a second embodiment, and the thin-blade chisel 30 employed in the second embodiment. The hammering direction changing tool 50 is the same as that of the first embodiment, and is therefore omitted.

A simulation piece 40 is attached to the thin-blade chisel 30. The simulation piece 40 includes a simulation piece shaft portion 41 and a simulation piece blade tip 42. The shape of the simulation piece shaft portion 41 is similar to that of the shaft portion 34 of the thin-blade chisel 30, and the shape of the simulation piece blade tip 42 is substantially the same as that of the blade tip 35 of the thin-blade chisel 30. A post 37 is formed on the thin-blade chisel 30, and a simulation piece engaging hole 43 is formed on the simulation piece 40, so that when the post 37 is engaged with the simulation piece engaging hole 43, the simulation piece 40 can be oriented parallel to the shaft portion 34 of the thin-blade chisel 30. The simulation piece 40 is attached such that the leading end of the blade tip 35 of the thin-blade chisel 30 and the leading end of the simulation piece blade tip 42 are located at the same position in the direction of the longitudinal axis.

The simulation piece 40 includes a simulation piece through hole 44. This through hole is provided for the same purpose as that of the through hole 36 of the thin-blade chisel 30. The extracting projection 57 of the hammering direction changing tool 50 is inserted in, and engaged with, the through hole 44 when the thin-blade chisel 30 is to be extracted from the medullary cavity.

FIG. 10 is a side view of the thin-blade chisel 30 employed in the thin-blade chisel system according to the second embodiment. The distance between the simulation piece 40 and the thin-blade chisel 30 is determined by adjusting the length of the post 37.

FIG. 11 illustrates the thin-blade chisel 30 employed in the thin-blade chisel system according to the second embodiment, cutting apart the interface at the proximal inner portion 11 of the hip joint stem 3 buried in the femur 1. Since the leading end of the simulation piece blade tip 42 is located outside the femur, the surgeon can recognize the position of the leading end of the blade tip 35, in view of the leading end of the simulation piece blade tip 42. Providing a light emitting element 45, such as a light emitting diode (LED), at the leading end of the simulation piece blade tip 42 enables the surgeon to recognize the position of the leading end of the blade tip 35 easily, even when the corresponding diseased part is narrow and dark.

Figure 12:
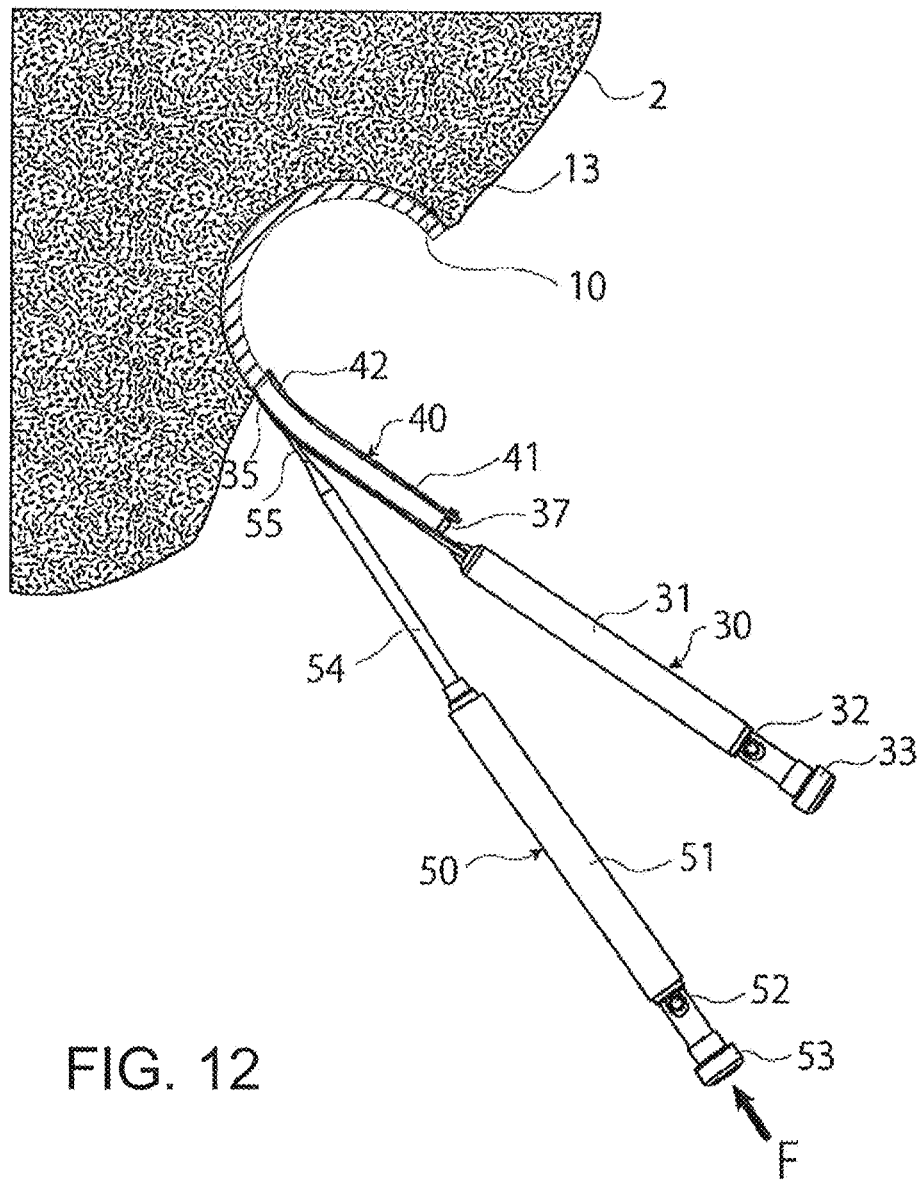
FIG. 12 is a schematic drawing showing a state where the system according to the present invention is about to separate an interface between the outer surface of a metal shell on the side of an acetabular roof, attached to the pelvis, and the inner surface of the acetabular roof.

FIG. 12 schematically illustrates a state where the thin-blade chisel system according to a third embodiment is about to separate the bone-conglutinated part 13 between the pelvis 2 and the metal shell 10 buried in the pelvis 2. With the third embodiment also, the interface between the implant and the bone, firmly combined to each other, can be efficiently separated, with the bone preserved unharmed, as with the first and second embodiments.

FIGS. 13 to 19 are perspective views, each showing a variation of the thin-blade chisel employed in the thin-blade chisel system according to the present invention. The illustrated examples of the thin-blade chisel have the blade tips of different shapes, according to the position where the chisel is used.

Figure 13:
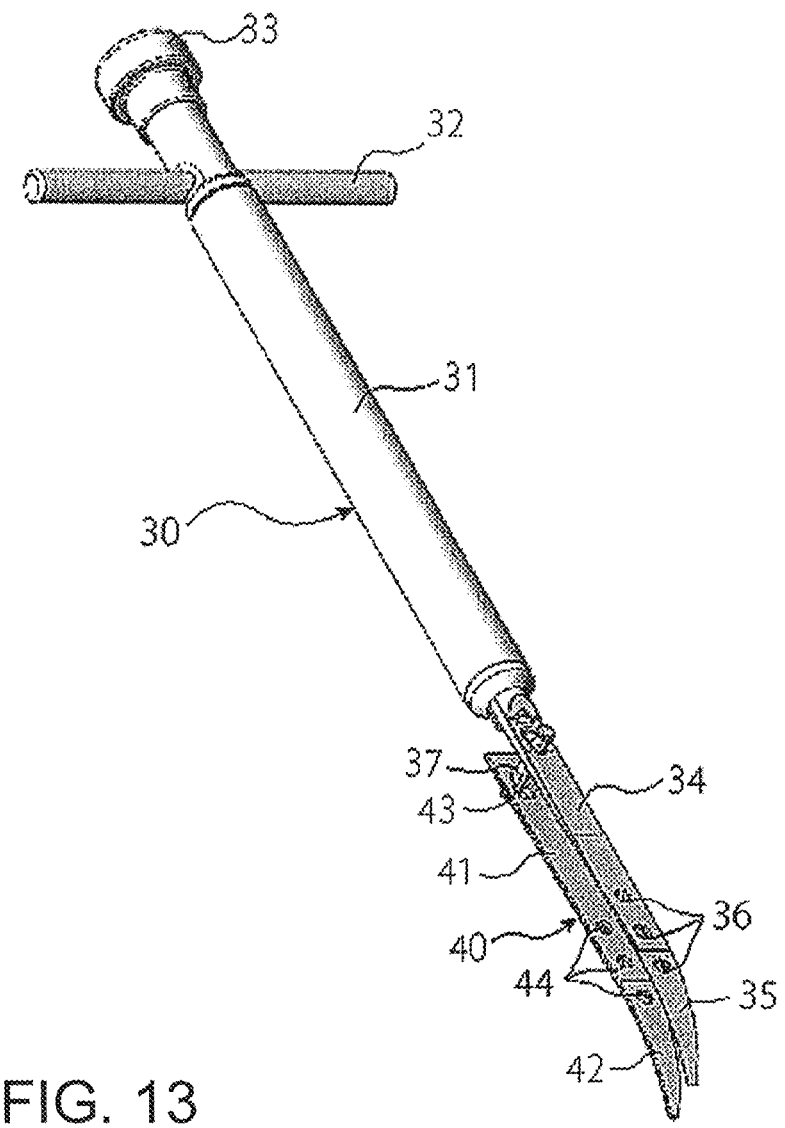
FIG. 13 is a perspective view showing a "thin horizontally curved straight chisel A", one of the variations of the thin-blade chisel.

In a thin horizontally curved straight chisel shown in FIG. 13, the blade tip is curved in the horizontal direction, and the surface of the blade is flat. Three through holes 36 are formed, and the implant and the bone can be efficiently separated from each other by hammering the hammering direction changing tool 50, with the recess 56 at the leading end of the hammering direction changing tool 50 fitted into one of the through holes 36.

Figure 14:
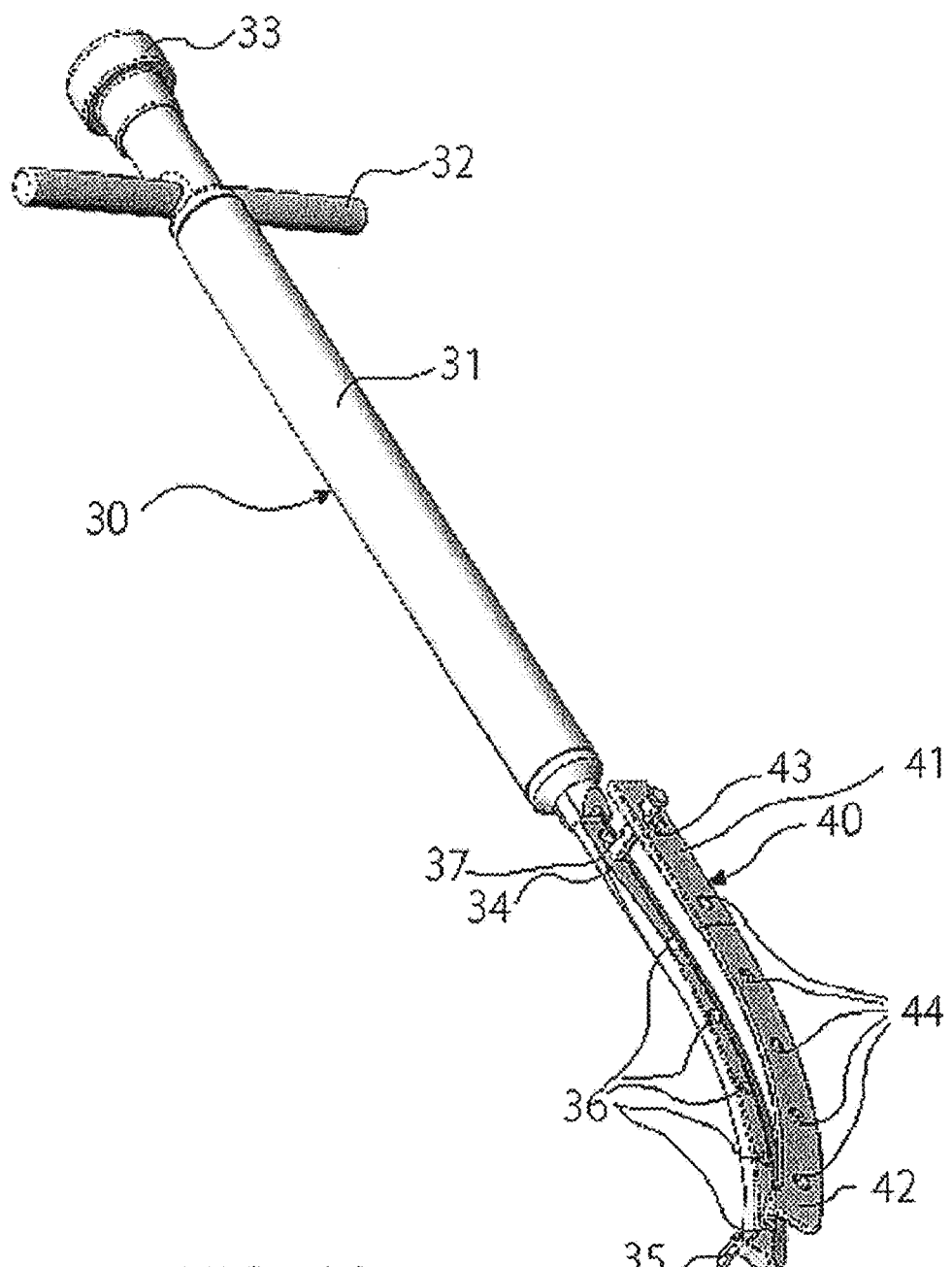
FIG. 14 is a perspective view showing a "thin horizontally curved straight chisel B", one of the variations of the thin-blade chisel.

In a thin horizontally curved straight chisel shown in FIG. 14, the blade tip is curved in the horizontal direction, and the surface of the blade is flat. Four through holes 36 are formed, and the implant and the bone can be efficiently separated from each other by hammering the hammering direction changing tool 50, with the recess 56 at the leading end of the hammering direction changing tool 50 fitted into one of the through holes 36.

Figure 15:
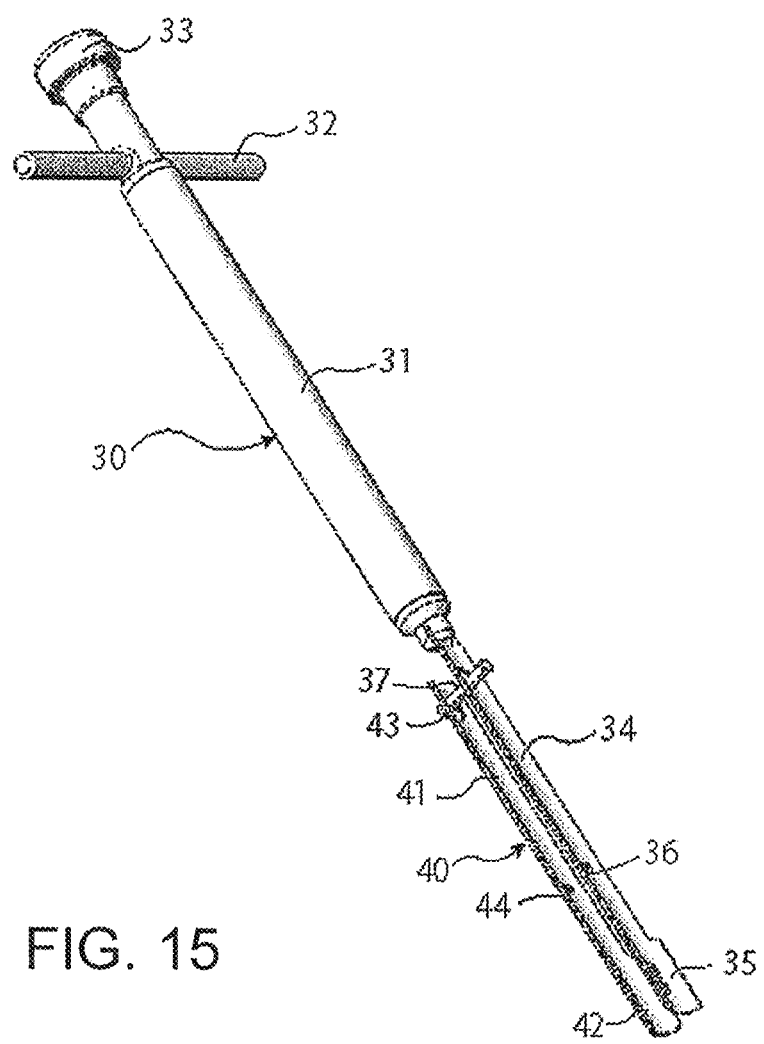
FIG. 15 is a perspective view showing a "curved-blade straight chisel", one of the variations of the thin-blade chisel.

In a curved-blade straight chisel shown in FIG. 15, the blade tip is curved in a transverse direction, and the surface of the blade is curved. The axis in the longitudinal direction is not curved but straight. A single through hole 36 is formed, and the implant and the bone can be efficiently separated from each other by hammering the hammering direction changing tool 50, with the recess 56 at the leading end of the hammering direction changing tool 50 fitted into the through hole 36.

Figure 16:
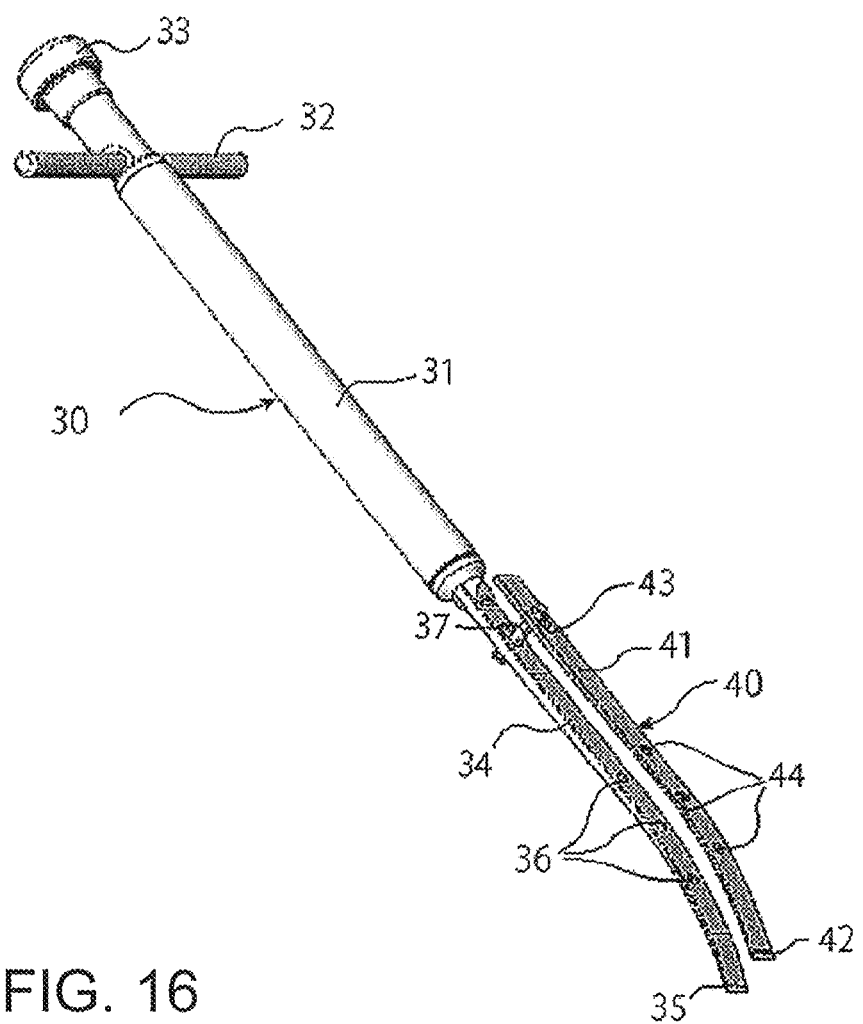
FIG. 16 is a perspective view showing a "tilted and curved straight chisel", one of the variations of the thin-blade chisel.

In a tilted and curved straight chisel shown in FIG. 16, the blade tip is tilted forward and curved, and the surface of the blade is flat. Three through holes 36 are formed, and the implant and the bone can be efficiently separated from each other by hammering the hammering direction changing tool 50, with the recess 56 at the leading end of the hammering direction changing tool 50 fitted into one of the through holes 36.

Figure 17:
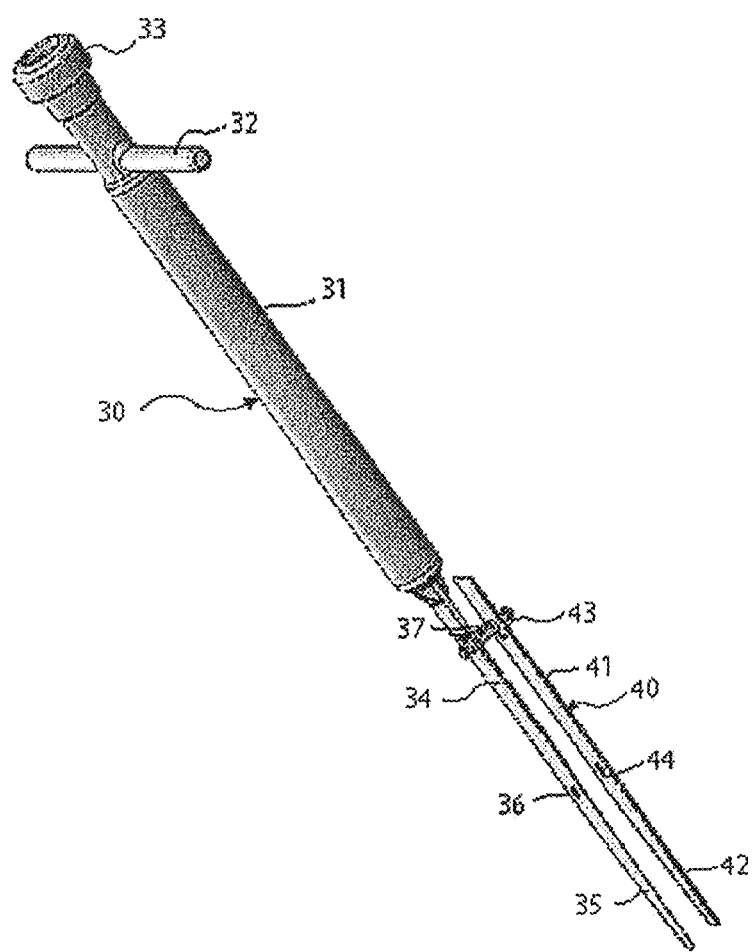
FIG. 17 is a perspective view showing a "straight chisel", one of the variations of the thin-blade chisel.

In a straight chisel shown in FIG. 17, the axis in the longitudinal direction is not curved but straight, and the surface of the blade is flat. A single through hole 36 is formed, and the implant and the bone can be efficiently separated from each other by hammering the hammering direction changing tool 50, with the recess 56 at the leading end of the hammering direction changing tool 50 fitted into the through hole 36.

Figure 18:
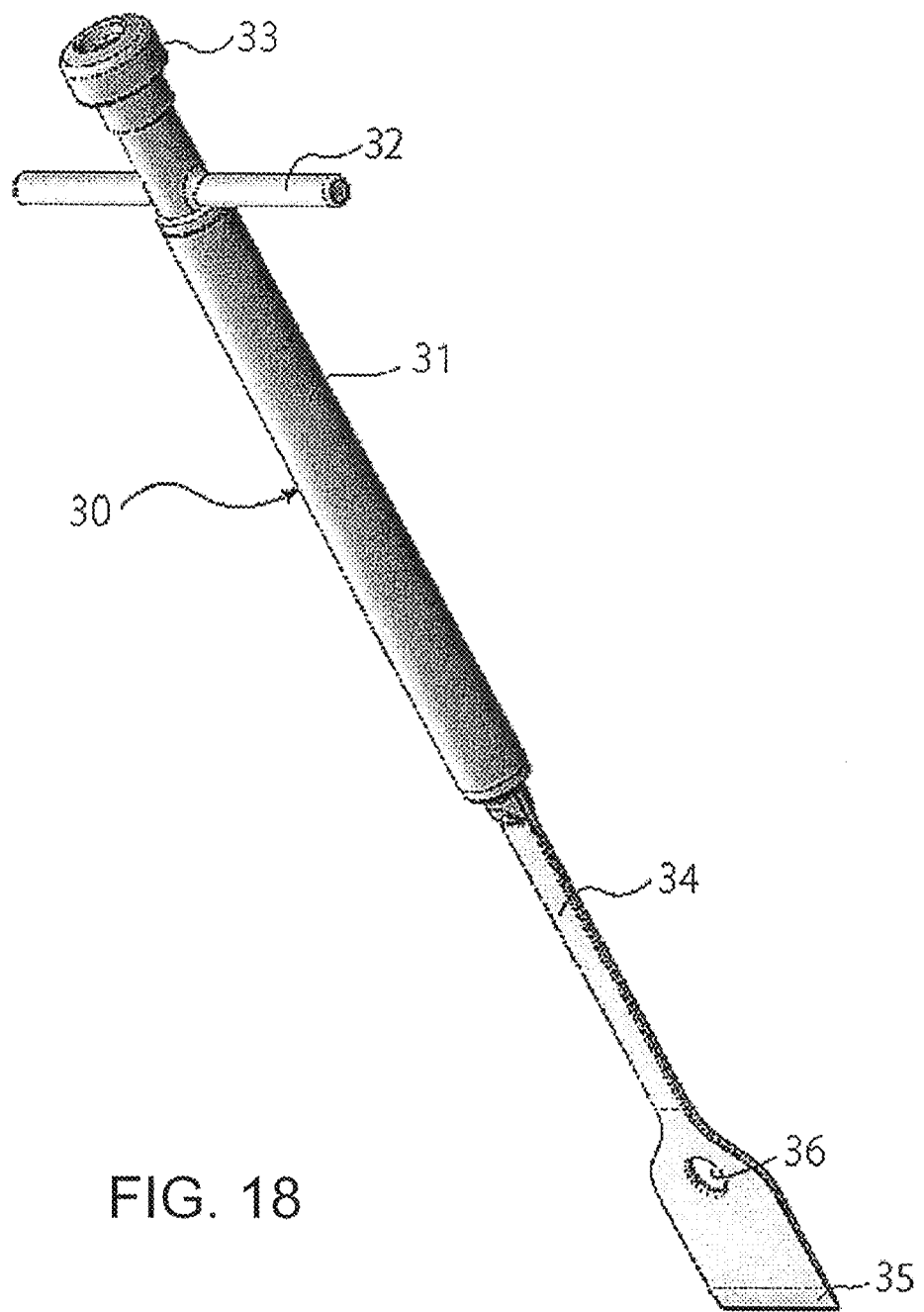
FIG. 18 is a perspective view showing a "wide straight chisel", one of the variations of the thin-blade chisel.

In a wide straight chisel shown in FIG. 18, the axis in the longitudinal direction is not curved but straight, and the surface of the blade is flat. The blade is formed in the leading end portion, which is formed in a wide shape. A single through hole 36 is formed, and the implant and the bone can be efficiently separated from each other by hammering the hammering direction changing tool 50, with the recess 56 at the leading end of the hammering direction changing tool 50 fitted into the through hole 36.

Figure 19:
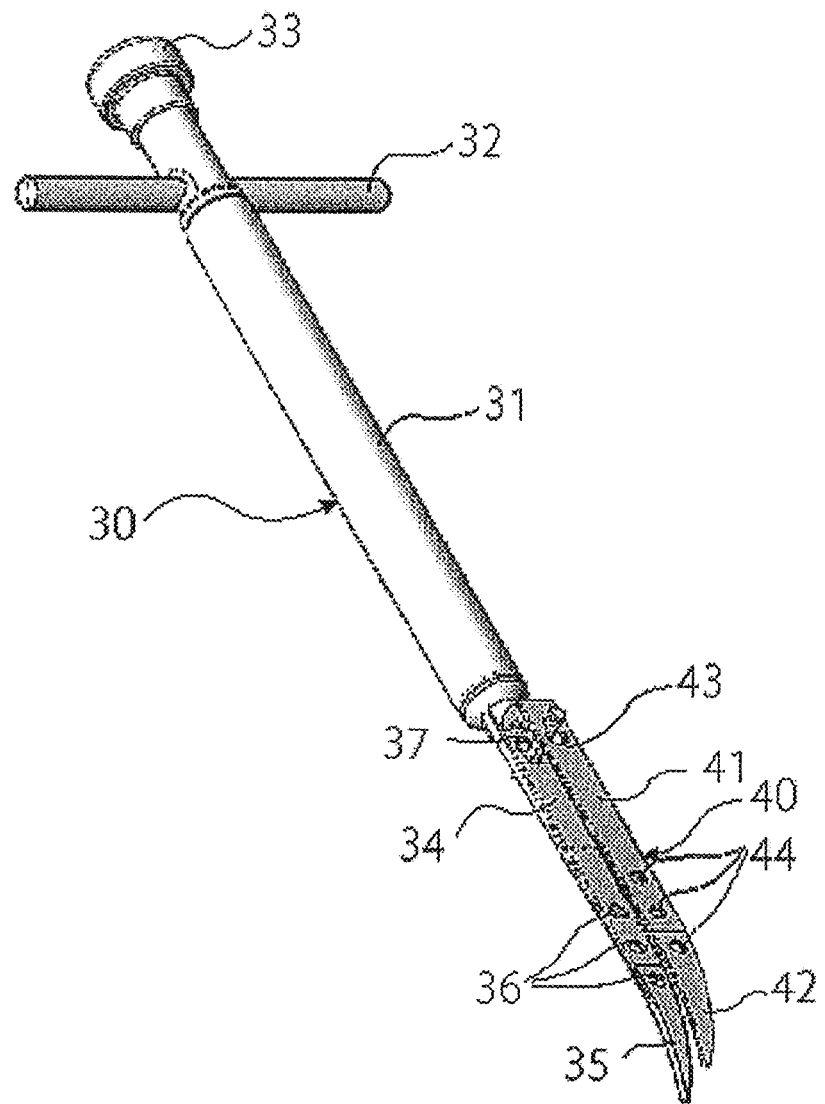
FIG. 19 is a perspective view showing a "single-blade horizontally curved chisel", one of the variations of the thin-blade chisel.

In a single-blade horizontally curved chisel shown in FIG. 19, the blade tip is curved in the horizontal direction, and the surface of the blade is flat. Three through holes 36 are formed, and the implant and the bone can be efficiently separated from each other by hammering the hammering direction changing tool 50, with the recess 56 at the leading end of the hammering direction changing tool 50 fitted into one of the through holes 36.

Figure 20:
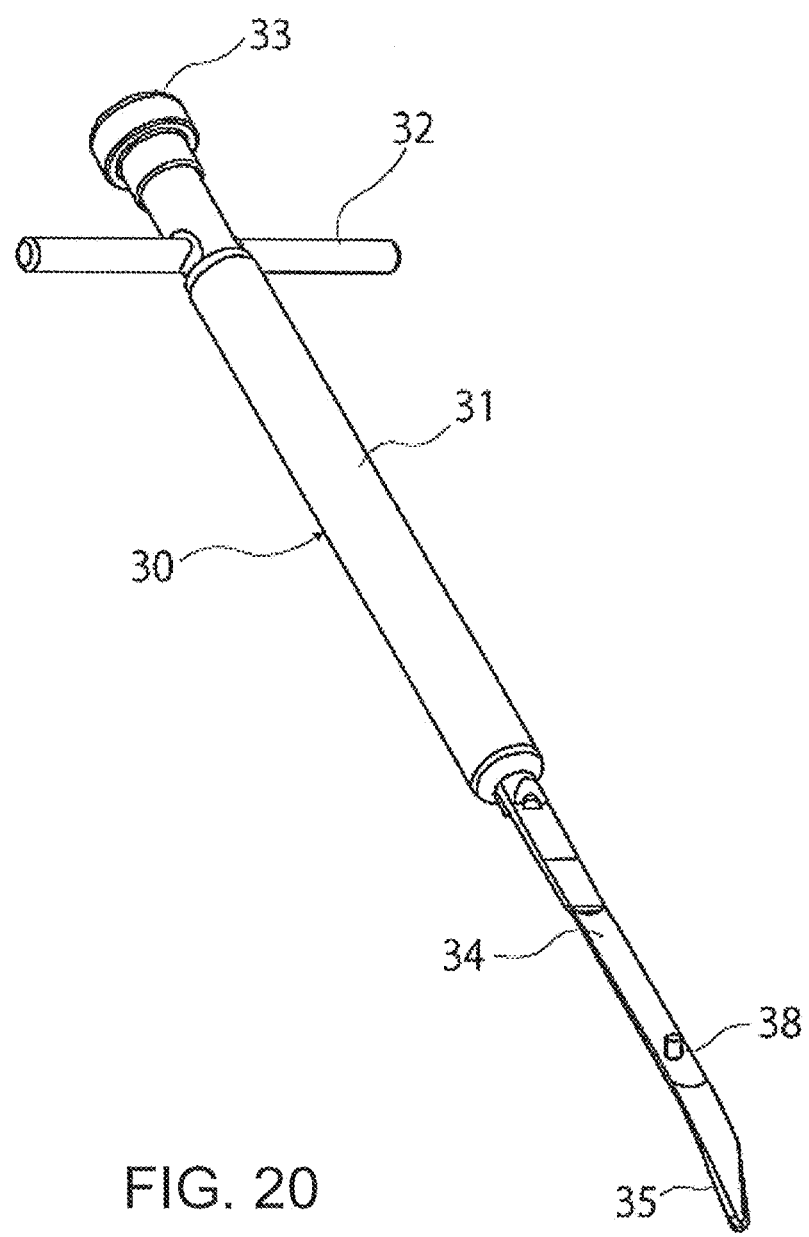
FIG. 20 is a perspective view showing a thin-blade chisel having an engaging projection instead of an engaging through hole.
Figure 21:
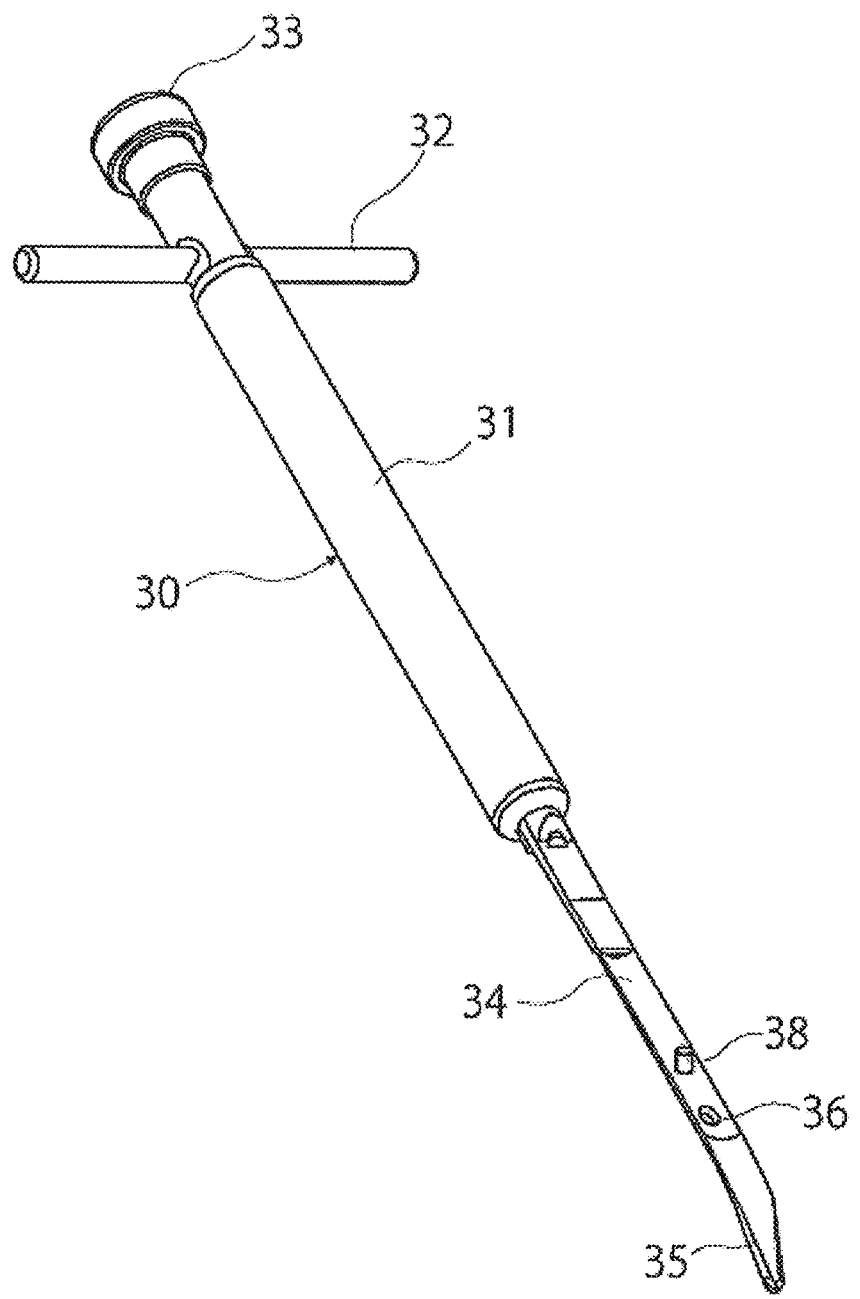
FIG. 21 is a perspective view showing a thin-blade chisel having the engaging through hole and the engaging projection.

FIG. 20 illustrates a thin-blade chisel 30, having an engaging projection 38 instead of the engaging through hole 36. FIG. 21 illustrates a thin-blade chisel 30 having both an engaging through hole 36 and an engaging projection 38. By engaging the recess 56 of the hammering direction changing tool 50 with the engaging projection 38, the hammering direction can be easily changed. When both of the engaging through hole 36 and the engaging projection 38 are provided as shown in FIG. 21, the interface between the implant and the bone firmly combined to each other can be more easily separated efficiently and safely, by using the engaging through hole 36 to hammer the hammering direction changing tool 50, and then engaging the recess 56 with the engaging projection 38 when the blade tip has intruded to a certain depth.

Figure 22:
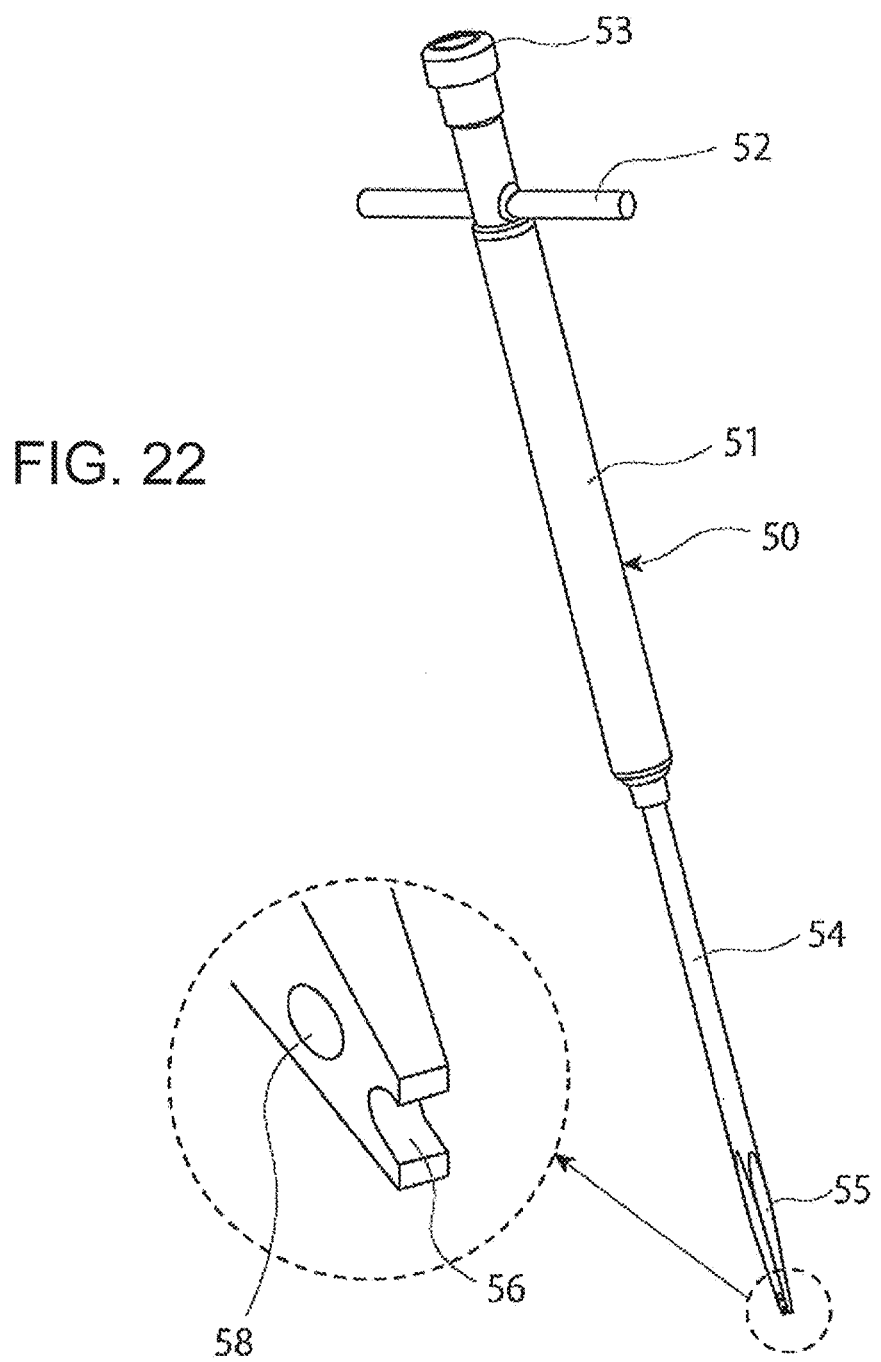
FIG. 22 is a perspective view showing a hammering direction changing tool having an extracting through hole.

FIG. 22 is a perspective view showing the hammering direction changing tool 50 having an extracting through hole 58. By inserting the engaging projection 38 in the extracting through hole 58, and hammering the handle 52 from the distal side toward the proximal side, the thin-blade chisel 30 can be easily extracted from inside the bone.

Figure 23:
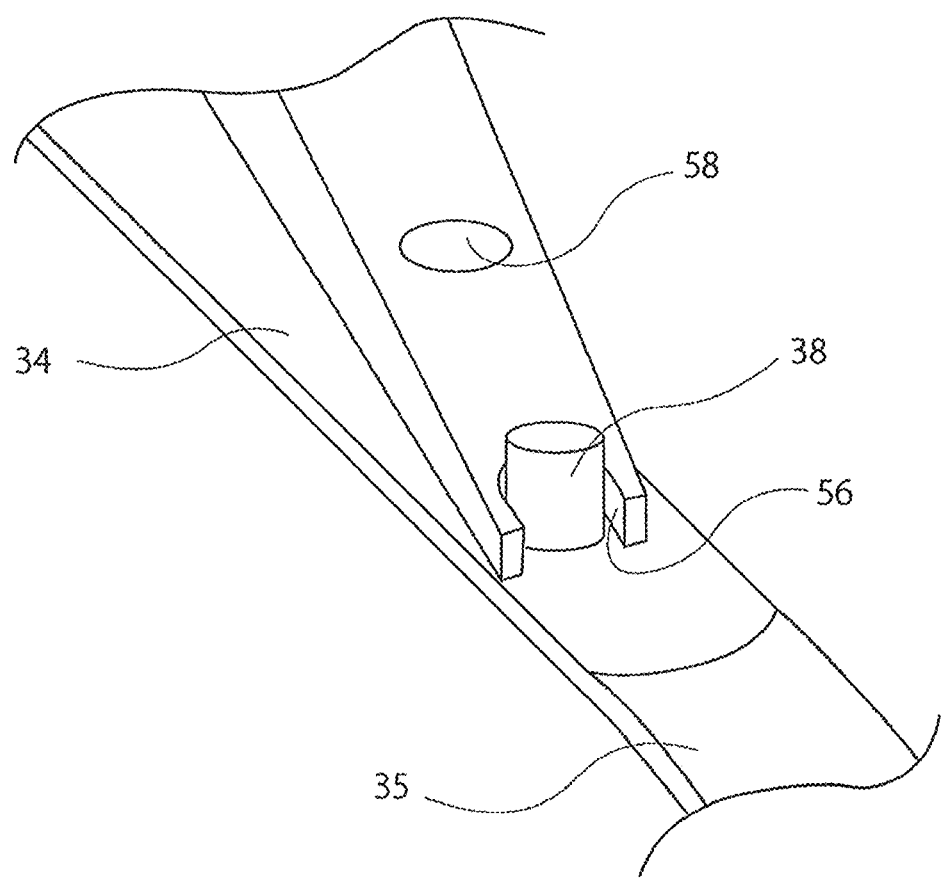
FIG. 23 is an enlarged perspective view showing the recess at the leading end of the hammering direction changing tool, engaged with the engaging projection of the thin-blade chisel.
Figure 24:
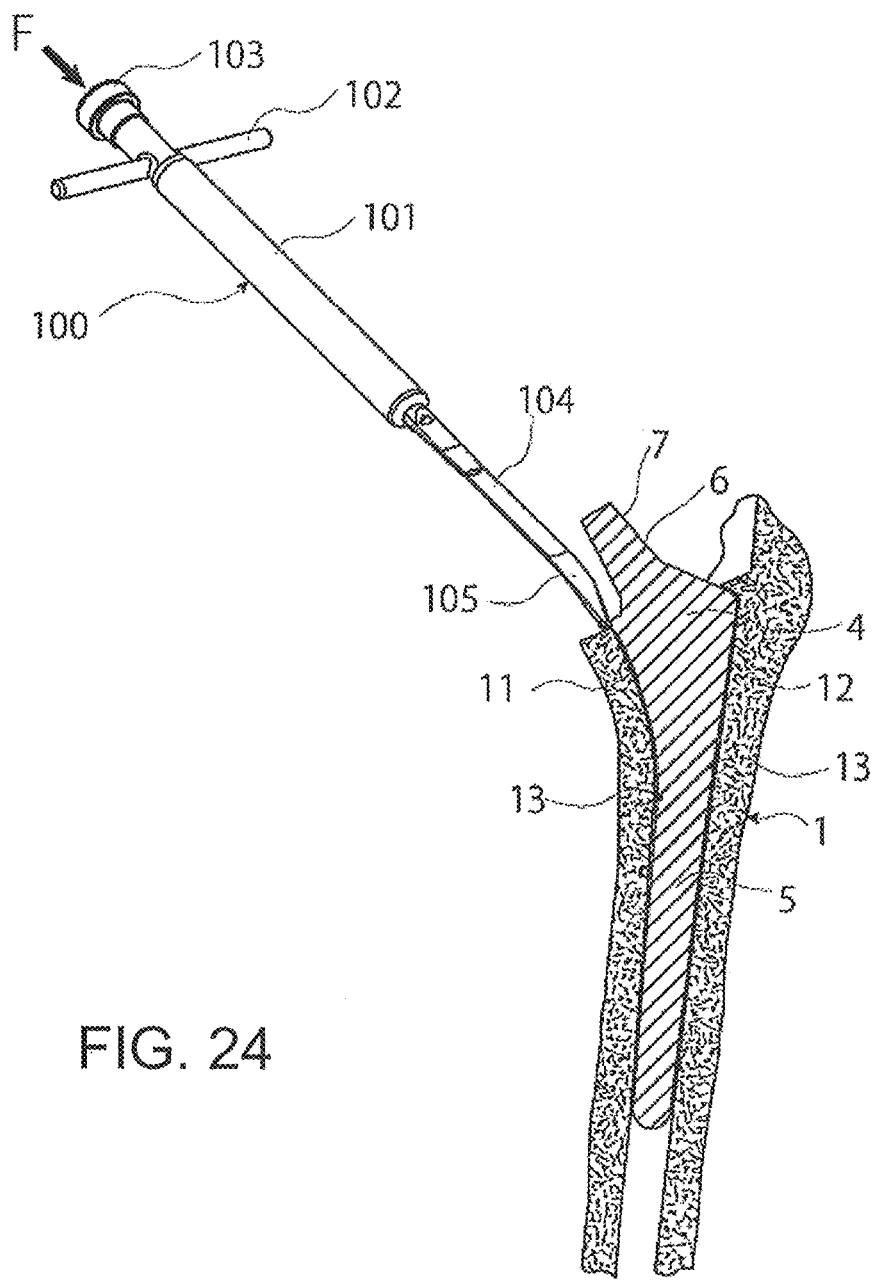
FIG. 24 is a schematic drawing showing an existing thin-blade chisel system, about to start separating the interface between the inner proximal portion of the hip joint stem and the bone.
Figure 25:
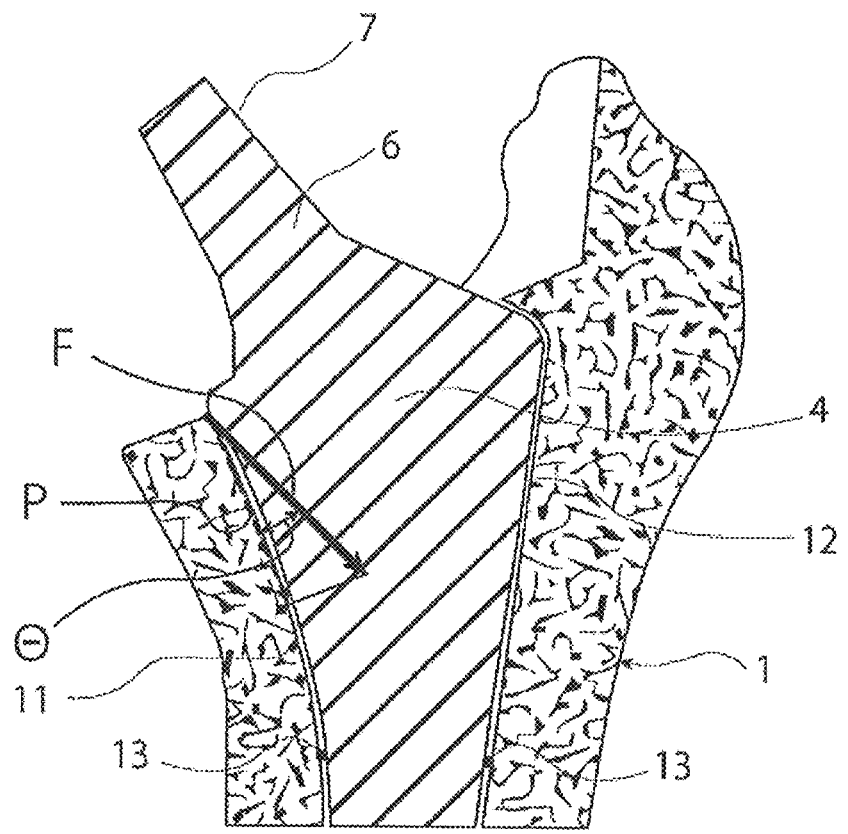
FIG. 25 is a schematic drawing showing a direction in which the force F is applied, and the intruding direction P of the blade tip, when the interface between the inner proximal portion of the hip joint stem and the bone is separated, using the existing thin-blade chisel system.

FIG. 23 is a schematic perspective view showing the recess 56 of the hammering direction changing tool 50 engaged with the engaging projection 38. By thus engaging the recess 56 with the engaging projection 38, the hammering direction can be easily changed.

INDUSTRIAL APPLICABILITY

The thin-blade chisel system according to the present invention can be advantageously utilized for a revision surgery, to separate the firmly combined interface between the implant and the bone efficiently and safely.

NUMERALS 1 femur
2 pelvis
3 hip joint stem
4 proximal portion
5 distal portion
6 neck portion
7 tapered portion
8 caput sphere
9 resin liner
10 metal shell
11 proximal inner portion
12 proximal outer portion
13 bone-conglutinated part
14 tissue in medullary cavity
30 thin-blade chisel
31 holding shaft portion
32 handle
33 hammering portion
34 shaft plate
35 blade tip
36 through hole
37 post
38 engaging projection
40 simulation piece
41 simulation piece shaft portion
42 simulation piece blade tip
43 simulation piece engaging hole
44 simulation piece through hole
45 light emitting element
50 hammering direction changing tool
51 holding shaft portion
52 handle
53 hammering portion
54 leading shaft portion
55 leading end portion
56 recess
57 extracting projection
58 extracting through hole

The invention claimed is:

1. A thin-blade chisel system for separating an outer surface of an orthopedic implant implanted inside a bone and an inner surface of the bone from each other, the thin-blade chisel system comprising:
    a thin-blade chisel having proximal and distal ends and a blade tip with an edge formed at said distal end; and
    a hammering direction changing tool engageable with the thin-blade chisel to apply a force in an advancing direction of the blade tip; wherein
    the thin-blade chisel has opposite surfaces extending in a proximal direction from said distal end, and a hammering blow-receiving through hole at a location spaced proximally from the blade tip but closer to the distal end of the chisel than to the proximal end thereof;
    said hammering blow-receiving through hole penetrates through said thin blade chisel from one of said opposite surfaces to the other in a direction of a thickness of said thin blade chisel;
    said thin blade chisel has a substantially straight portion extending along a chisel axis from said through hole to said proximal end;
    said hammering direction changing tool is substantially straight, with a hammering direction changing tool axis extending from a distal end portion to a proximal end portion of said hammering direction changing tool, and includes a hammering portion located at a said proximal end portion and a recess formed at a said distal end portion, said hammering portion having a surface facing in a proximal direction of the hammering direction changing tool and being engageable by a hammer blow directed in the distal direction of the hammering direction changing tool, said recess being configured to be engaged with said hammering blow-receiving through hole,
    said recess is formed in a shape that allows engagement of said recess with both of said opposite surfaces at opposite ends of said through hole while said hammering direction changing tool axis extends in an oblique direction relative to said chisel axis; and
    the edge of the thin-blade chisel is configured to intrude between an outer surface of an orthopedic implant and an inner surface of a bone along a curved path defined by the inner surface of said bone by hammering said hammering portion—with the recess of the hammering direction changing tool engaged with the hammering blow-receiving through hole of the thin-blade chisel while said hammering direction changing tool axis extends in said oblique direction relative to said chisel axis.

2. The thin-blade chisel system according to claim 1, wherein the hammering direction changing tool includes an extracting projection formed in a vicinity of the recess, and a bar shaped handle formed in a vicinity of the hammering portion and extending in a direction perpendicular to said hammering direction changing tool axis, said bar-shaped handle having a proximal side and a distal side, the extracting projection being configured to be inserted in into said through hole, and the bar-shaped handle being configured so that the thin-blade chisel can be extracted by inserting the extracting projection into the through hole and hammering the bar-shaped handle from a said distal side toward a said proximal side.

3. The thin-blade chisel system according to claim 1, wherein said thin blade chisel has a curved portion extending from said edge formed at said distal end, whereby said blade tip is directed in an oblique direction relative to said chisel axis, and wherein said recess formed at the distal end portion of said hammering direction changing tool is configured to engage with both of said opposite surfaces of said thin blade chisel when engaged with said hammering blow-receiving through hole while said hammering direction changing tool axis is substantially parallel to the oblique direction in which said blade tip is directed.

* * * * *